United States Patent [19]

Corfield et al.

[11] 4,176,231

[45] Nov. 27, 1979

[54] PROCESS FOR PREPARING 3-EXOMETHYLENECEPHAM SULFOXIDES

[75] Inventors: John R. Corfield, Runcorn; Clifford G. Taylor, Warrington, both of England

[73] Assignee: Lilly Industries Limited, London, United Kingdom

[21] Appl. No.: 911,621

[22] Filed: Jun. 1, 1978

[30] Foreign Application Priority Data

Dec. 24, 1977 [GB] United Kingdom ............... 53897/77

[51] Int. Cl.$^2$ ............................................. C07D 501/04
[52] U.S. Cl. ..................................... 544/16; 424/246; 544/30; 544/22
[58] Field of Search ........................ 544/22, 28, 30, 16

[56] References Cited

U.S. PATENT DOCUMENTS

| 3,932,393 | 1/1976 | Chavvette | 544/30 |
| 4,013,650 | 3/1977 | Fechtig | 544/16 |
| 4,060,688 | 11/1977 | Chavvette | 544/16 |

FOREIGN PATENT DOCUMENTS 50-63480  12/1976  Japan .
51-19620  8/1977  Japan .

*Primary Examiner*—Nicholas S. Rizzo
*Attorney, Agent, or Firm*—Steven R. Lammert; Arthur R. Whale

[57] ABSTRACT

3-Exomethylenecepham sulfoxides are prepared by the reaction of 3-methyl-3-halocepham sulfoxides with mercuric or mercurous perchlorate.

4 Claims, No Drawings

PROCESS FOR PREPARING 3-EXOMETHYLENECEPHAM SULFOXIDES

BACKGROUND AND SUMMARY OF THE INVENTION

3-Exomethylenecephams are of great value as intermediates in the synthesis of cephalosporin antibiotics. Most recently, 3-exomethylenecepham sulfoxides have been employed to prepare 3-acetoxymethylcephem compounds (U.S. Pat. No. 4,029,651 issued June 14, 1977) and 3-chloro cephems (U.S. Pat. No. 3,925,372 issued Dec. 9, 1975). The demonstrated versatility of 3-exomethylenecephams as intermediates to cephem antibiotic compounds has prompted a continuing investigation into new synthetic routes to these intermediates.

3-Exomethylenecepham intermediates have been prepared from cephalosporanic acids by first treating the cephalosporanic acids with selected sulfur nucleophiles such as thiourea, thiobenzoic acid or potassium ethyl xanthate and then reducing the respective product $C_3$-(substituted)-thiomethylcephems with either Raney nickel in aqueous ethanol or zinc in formic acid-dimethylformamide. More recently 3-exomethylenecepham intermediates have been prepared by the acid catalyzed cyclization of certain penicillin sulfoxide derived azetidinone sulfinyl chlorides (S. Kukolja, et al., *Journal of the American Chemical Society*, 98, 5040 (1976).

This invention relates to the novel preparation of 3-exomethylenecepham sulfoxides by the reaction of 3-halo-3-methylcepham sulfoxides with mercuric or mercurous perchlorate.

DETAILED DESCRIPTION OF THE INVENTION

In the process of the present invention a 3-exomethylenecepham compound of the formula

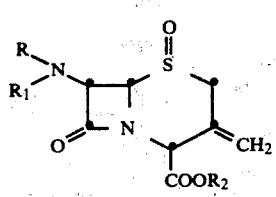

is prepared by reacting a 3-halo-3-methylcepham sulfoxide of the formula

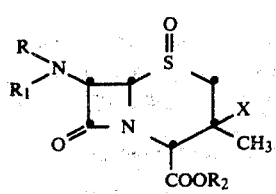

with mercuric or mercurous perchlorate in an inert organic solvent wherein the above formula R and $R_1$ are independently hydrogen or an acyl group derived from a carboxylic acid, $R_2$ is a carboxylic acid protecting group and X is bromine or iodine.

The C-7 side chain group of the formula

includes amino and those conventional acyl amino groups in the β-lactam art; the nature of R and $R_1$ is not critical in the present process since these moieties are far removed from the reaction site, i.e., the 3-position of the cepham nucleus. Thus, for example, R can be hydrogen and $R_1$ can be a carboxylic acid derived acyl group of the formula

wherein $R_3$ is
(a) hydrogen, $C_1$–$C_3$ alkyl, halomethyl, cyanomethyl or 3-(2-chlorophenyl)-5-methylisoxazol-4-yl;
(b) benzyloxy, 4-nitrobenzyloxy, 2,2,2-trichloroethoxy, tert-butoxy, or 4-methoxybenzyloxy;
(c) the group R'' wherein R'' is phenyl or phenyl substituted with 1 or 2 substituents independently selected from the group consisting of halo, protected hydroxy, nitro, cyano, trifluoromethyl, $C_1$–$C_3$ alkyl, and $C_1$–$C_4$ alkoxy;
(d) an arylalkyl group of the formula

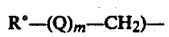

wherein R° is R'' as defined above, 2-thienyl, 3-thienyl, or 1,4-cyclohexyldienyl, m is 0 or 1, and Q is O or S subject to the limitation that when m is 1 R° is R'';
(e) a substituted arylalkyl group of the formula

wherein R° is as defined above and W is hydroxy, protected hydroxy, amino, protected amino, or protected carboxy; or
(f) a heteroarylmethyl group of the formula $R_4CH_2$— wherein $R_4$ is 2-furyl, 3-furyl, 2-thiazolyl, 5-isoxazolyl, or 5-tetrazolyl.

Alternatively R and $R_1$ of the C-7 group

can each be an acyl group of the formula

wherein $R_3$ is as defined above, to form an acylic imido group; or R and $R_1$ taken together with the nitrogen atom to which they are attached can form an cyclic imido group of the formula

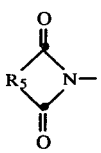

wherein R₅ is $C_2$–$C_4$ alklene, $C_2$–$C_4$ alkenylene, 1,2-phenylene, or 1,2-cyclohexenylene.

In the foregoing description of the present invention the term "$C_1$–$C_3$ alkyl" refers to methyl, ethyl, n-propyl or isopropyl. Representative "$C_1$–$C_4$ alkoxy" groups are methoxy, ethoxy, n-propoxy, and tert-butoxy. "Halomethyl" represents chloromethyl, bromomethyl, fluoromethyl and iodomethyl. Imido groups represented when R₅ is $C_2$–$C_4$ alkylene are succinimido, 3-methylsuccinimido and 3,4-dimethylsuccinimido. Exemplary of imido groups when R₅ is $C_2$–$C_4$ alkenylene are maleimido, 3-ethylmaleimido, 3-methylmaleimido, and 3,4-dimethylmaleimido. When R₅ is 1,2-cyclohexenylene or 1,2-phenylene the imido groups represented are tetrahydrophthalimido and phthalimido respectively.

When in the above definition R″ represents a substituted phenyl group, R″ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydroxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or dialkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R″ represents disubstituted phenyl groups wherein the substituents are different for example, 3-methyl-4-methoxyphenyl, 3-chloro-4-benzyoxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$–$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$–$C_3$ alkyl)silyl, succinimidomethyl and like ester forming moieties. Other known carboxy protecting groups such as those described by E. Haslam in "Protective Groups in Organic Chemistry", supra, Chapter 5, shall be recognized as suitable. The nature of such ester forming groups is not critical In the foregoing definitions, hydroxy, amino, and carboxy protecting groups are not exhaustively defined. The function of such groups is to protect the reactive functional groups, for example, during the preparation of the starting materials, and to then be removed at some later point in time without disrupting the remainder of the molecule. Many such protective groups are well known in the art and the use of other groups equally applicable to the process and compounds of the present invention shall be recognized as suitable. Thus, there is no novelty or inventiveness asserted with regard to the "protecting groups" alluded to in this specification.

Representative of the acylamino group,

as defined hereinabove are formamido, acetamido, propionamide, butyramido, 2-pentenoylamino, cyanoacetamido, chloroacetamido, bromoacetamido, 5-tert-butoxycarbonylamino-5-tert-butoxycarbonylvaleramido, and the like.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when R₃ is a group of the formula R°(Q)$_m$CH₂— and m is O, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido, 2-thienylacetamido, 3-thienylacetamido and the like; and when m is 1 and Q is O, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups; and when m is 1 and Q is S, representative groups are phenylthioacetamido, 2,5-dichlorophenylthioacetamido, 4-bromophenylthioacetamido, 4-methoxyphenylthioacetamido, 4-tolylthioacetamido and like substituted phenylthioacetamido groups.

Illustrative of the acylamino groups when $R_3$ is a substituted arylalkyl group of the formula

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyoxyl-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)acetamido and like groups.

Exemplary of the acylamino group

when $R_3$ is a heteroarylmethyl group of the formula $R_4$—$CH_2$— are 2-furylacetamido, 3-furylacetamido, a 2-thiazolylacetamido group of the formula

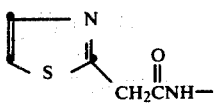

or a 5-isoxazolylacetamido group of the formula

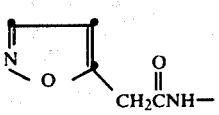

The 3-halo-3-methylcepham sulfoxide starting materials for the present process are either known or can be prepared by the oxidation of the corresponding 3-halo-3-methylcepham compounds described, for example in U.K. Patent Specification Nos. 1,403,001, 1,445,845, and 1,453,301, by conventional oxidation procedures such as by the utilization of m-chloroperbenzoic acid in a suitable organic solvent. It has been found that the conversion of the present invention proceeds irrespective of whether the sulfoxide part of the molecule is in the α-or β-stereo configuration.

The mercury salts which effect the chemical conversion of the present process are mercuric perchlorate and mercurous perchlorate. The amount of mercury salt utilized is typically such as to provide at least about one molar equivalent of mercury salt per mole of 3-halo-3-methylcepham sulfoxide starting material. Preferably about a 10 percent molar excess of the mercury salt is employed.

The present process is carried out in an inert organic solvent. By "inert organic solvent" is meant an organic solvent which, under the conditions of the present process, does not enter into any appreciable reaction with either the reactants or the products. Any of a wide variety of common aprotic organic solvents can be utilized. Suitable organic solvents for use in connection with the process of the invention include ethereal solvents such as 1,2-dimethoxyethane, tetrahydrofuran and 1,4-dioxane; ketonic solvents such as acetone, and nitrile solvents such as acetonitrile. 1,2-Dimethoxyethane is the presently preferred solvent.

Temperature is not a critical reaction parameter so long as it is appreciated that high temperatures can cause decomposition of the cephem nucleus. In general, the reaction can be accomplished at temperatures within the range from 0° to 100° C., preferably at ambient temperature.

The products produced in accordance with the process of this invention can be isolated and purified by employing conventional laboratory techniques. These include chromatographic separation, filtration, crystallization recrystallization and like methods.

As described hereinabove the products of the present process are known versatile intermediates in the preparation of clinically significant cephalosporin antibiotics.

The present invention will now be further illustrated with reference to the following non-limitative Examples in which Examples 1 to 3 relate to the preparation of starting materials of use in the process of the invention whereas Examples 4 to 9 illustrate the inventive process itself.

EXAMPLE 1 p-Nitrobenzyl 3β-bromo-3α-methyl-7β-phenoxyacetamidocepham-4α-carboxylate 1β-oxide Iodobenzene dichloride (10.2 g) was added to a stirred suspension of p-nitrobenzyl 3β-bromo-3α-methyl-7β-phenoxyacetamidocepham-4α-carboxylate (10.2 g) in a mixture of pyridine (135 ml) and water (15 ml) at −35° to −25° C. The mixture was stirred at −35° to −25° C. for 1 hour. The clear yellow solution was allowed to warm up to −10° C. and poured into a mixture of crushed ice and water. The mixture was extracted with chloroform. The extract was washed several times with dilute hydrochloric acid to remove all the remaining pyridine, and subsequently washed with water and dried over sodium sulphate. After removal of the solvent on a rotary evaporator, the red oily residue was crystallized from methanol to give p-nitrobenzyl 3β-bromo-3α-methyl-7β-phenoxyacetamidocepham-4α-carboxylate 1β-oxide (5.95 g), melting point 147°–149° C.

EXAMPLE 2 p-Nitrobenzyl 3β-bromo-3α-methyl-7β-phenoxyacetamdocepham-4α-carboxylate 1α-oxide A solution of m-chloroperbenzoic acid (2.81 g) in chloroform (30 ml) was added dropwise over 10 minutes to a solution of p-nitrobenzyl 3β-bromo-3α-methyl-7β-phenoxyacetamido-4α-carboxylate (9.2 g) in chloroform (50 ml) at 0° C. The mixture was stirred at 0° C. for 1 hour. The solution was extracted with a saturated aqueous sodium bicarbonate solution and then with water and dried over sodium sulphate. The solvent was distilled off on a rotary evaporator to give p-nitrobenzyl 3β-bromo-3α-methyl-7β-phenoxyacetamidocepham-4α-carboxylate 1α-oxide (8.4 g) as a friable white foam.

EXAMPLE 3 p-Nitrobenzyl 3β-iodo-3α-methyl-7β-phenoxyacetamidocepham-4α-carboxylate 1α-oxide A solution of m-chloroperbenzoic acid (0.34 g) in chloroform (20 ml) was added dropwise over 10 minutes to a solution of p-nitrobenzyl 3β-iodo-3α-methyl-7β-phenoxyacetamidocepham-4α-carboxylate (1.2 g) in chloroform (30 ml) at 0° C. The mixture was stirred for 1 hour at 0° C. The solution was washed with a saturated aqueous sodium bicarbonate solution and then with water and dried over sodium sulphate. The solvent was distilled off on a rotary evaporator to give p-nitrobenzyl 3β-iodo-3α-methyl-7β-phenoxyacetamidocepham-4α-carboxylate 1α-oxide as a friable pale yellow foam.

EXAMPLE 4 p-Nitrobenzyl 7β-phenoxyacetamido-3-methylenecepham-4α-carboxylate 1β-oxide

Mercurous perchlorate (330 mg) was added to a stirred solution of p-nitrobenzyl 3β-bromo-3α-methyl-7β-phenoxyacetamidocepham-4α-carboxylate 1β-oxide (580 mg) in 1,2-dimethoxyethane (50 ml). The reaction mixture was stirred at room temperature for 20 hours, filtered and the precipitate washed on the filter with chloroform. The filtrate and chloroform wash were combined and washed with saturated aqueous sodium bicarbonate followed by water. The organic solution was dried with sodium sulphate and the solvent removed on a rotary evaporator. The residual gum was crystallized from methanol to give white crystals of p-nitrobenzyl 7β-phenoxyacetamido-3-methylenecepham-4α-carboxylate 1β-oxide (382 mg), melting point 198°–200° C.

EXAMPLE 5 p-Nitrobenzyl 7β-phenoxyacetamido-3-methylenecepham-4α-carboxylate 1α-oxide

Mercurous perchlorate (660 mg) was added to a stirred solution of p-nitrobenzyl 3β-bromo-3α-methyl-7β-phenoxyacetamidocepham-4α-carboxylate 1α-oxide (1.16 g) in 1,2-dimethoxyethane (50 ml). The reaction mixture was stirred at room temperature for 20 hours, filtered and the precipitate washed on the filter with chloroform. The filtrate and chloroform wash were combined and washed with saturated aqueous sodium bicarbonate followed by water. The organic solution was dried with sodium sulphate and the solvent removed on a rotary evaporator. The residual gum was crystallized from methanol to give white crystals of p-nitrobenzyl 7β-phenoxyacetamido-3-methylenecepham-4α-carboxylate 1α-oxide (0.75 g), melting point 187°–189° C.

EXAMPLE 6 p-Nitrobenzyl 7β-phenoxyacetamido-3-methylenecepham-4α-carboxylate 1β-oxide

Mercurous pherchlorate (66 mg) was added to a solution of p-nitrobenzyl 3β-bromo-3α-methyl-7β-phenoxyacetamidocepham-4α-carboxylate 1β-oxide (115 mg) in acetone (10 ml). The reaction mixture was stirred at room temperature for 16 hours, filtered and the precipitate washed on the filter with chloroform. The filtrate and chloroform wash were combined and washed with saturated aqueous sodium bicarbonate followed by water. The organic solution was dried with sodium sulphate and the solvent removed on a rotary evaporator to give p-nitrobenzyl 7β-phenoxyacetamido-3-methylenecapham-4α-carboxylate 1β-oxide.

EXAMPLE 7 p-Nitrobenzyl 7β-phenoxyacetamido-3-methylenecepham-4α-carboxylate 1β-oxide

Mercuric perchlorate (90 mg) was added to a solution of p-nitrobenzyl 3β-bromo-3α-methyl-7β-phenoxyacetamidocepham-4α-carboxylate 1β-oxide (116 mg) in acetonitrile (15 ml). The mixture was refluxed for 1 hour, cooled to room temperature, filtered, and the precipitate washed on the filter with chloroform. The filtrate and chloroform wash were combined and washed with saturated aqueous sodium bicarbonate solution followed by water. The organic solution was dried with sodium sulphate and the solvent removed on a rotary evaporator. The residual gum was crystallized from methanol to give white crystals of p-nitrobenzyl 7β-phenoxyacetamido-3-methylenecepham-4α-carboxylate 1β-oxide.

EXAMPLE 8 p-Nitrobenzyl 7β-phenoxyacetamido-3-methylenecepham-4α-carboxylate 1α-oxide

Mercuric pherchlorate (220 mg) was added to a stirred solution of p-nitrobenzyl 3β-iodo-3α-methyl-7β-phenoxyacetamidocepham-4α-carboxylate 1α-oxide (314 mg) in 1,2-dimethoxyethane (15 ml). The reaction mixture was stirred at room temperature for 20 hours, filtered and the precipitate washed on the filter with chloroform. The filtrate and chloroform wash were combined and washed with saturated aqueous sodium bicarbonate followed by water. The organic solution was dried with sodium sulphate and the solvent removed on a rotary evaporator. The residual foam was crystallized from methanol to give white crystals of p-nitrobenzyl 7β-phenoxyacetamido-3-methylenecepham-4α-carboxylate 1α-oxide.

EXAMPLE 9 p-Nitrobenzyl 7β-phenoxyacetamido-3-methylenecepham-4α-carboxylate 1α-oxide

Mercurous perchlorate (165 mg) was added to a stirred solution of p-nitrobenzyl 3β-iodo-3α-methyl-7β-phenoxyacetamidocepham-4α-carboxylate 1α-oxide (314 mg) in 1,2-dimethoxyethane (15 ml). The reaction mixture was stirred at room temperature for 20 hours, filtered and the precipitate washed on the filter with chloroform. The filtrate and chloroform wash were combined and washed with saturated aqueous sodium bicarbonate followed by water. The organic solution was dried with sodium sulphate and the solvent removed on a rotary evaporator. The residual gum was purified by column chromatography on silica gel with chloroform as the eluant to give white crystals of p-nitrobenzyl 7β-phenoxyacetamido-3-methylenecepham-4α-carboxylate 1α-oxide (50 mg).

We claim:

1. A process for the preparation of a 3-exomethylenecepham sulfoxide of the formula

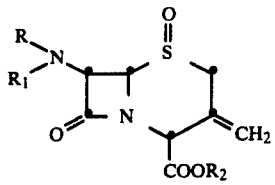

by reacting a 3-halo-3-methylcepham sulfoxide of the formula

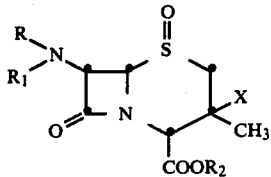

with mercuric or mercurous perchlorate in an inert organic solvent wherein the above formula R and $R_1$ are independently hydrogen or an acyl group derived from a carboxylic acid, $R_2$ is a carboxylic acid protecting group and X is bromine or iodine.

2. The process of claim 1 wherein R is hydrogen and $R_1$ is an acyl group derived from a carboxylic acid.

3. The process of claim 2 wherein the inert organic solvent is 1,2-dimethoxyethane, tetrahydrofuran, 1,4-dioxane, acetone, or acetonitrile.

4. The process of claim 3 wherein the inert organic solvent is 1,2-dimethoxyethane.

* * * * *